(12) United States Patent
Wang et al.

(10) Patent No.: US 12,220,269 B2
(45) Date of Patent: Feb. 11, 2025

(54) METHOD AND SYSTEM FOR VISUALIZING X-RAY POSITIONING OF HANDHELD X-RAY MACHINE

(71) Applicant: Shenzhen Browiner Tech Co., Ltd, Shenzhen (CN)

(72) Inventors: Anshan Wang, Shenzhen (CN); Fusheng Zhong, Shenzhen (CN); Hailong Tan, Shenzhen (CN)

(73) Assignee: Shenzhen Browiner Tech Co., Ltd, Shenzhen (CN)

( * ) Notice: Subject to any disclaimer, the term of this patent is extended or adjusted under 35 U.S.C. 154(b) by 224 days.

(21) Appl. No.: 17/980,786

(22) Filed: Nov. 4, 2022

(65) Prior Publication Data
US 2023/0337997 A1    Oct. 26, 2023

(30) Foreign Application Priority Data
Apr. 20, 2022    (CN) .......................... 202210413517.8

(51) Int. Cl.
*A61B 6/08*    (2006.01)
*A61B 6/00*    (2024.01)
*A61B 6/46*    (2024.01)
*A61B 6/50*    (2024.01)
*A61B 6/58*    (2024.01)

(52) U.S. Cl.
CPC .............. *A61B 6/08* (2013.01); *A61B 6/4405* (2013.01); *A61B 6/461* (2013.01); *A61B 6/505* (2013.01); *A61B 6/545* (2013.01); *A61B 6/52* (2013.01); *A61B 6/587* (2013.01)

(58) Field of Classification Search
CPC ......... A61B 6/08; A61B 6/4405; A61B 6/461; A61B 6/505; A61B 6/545
See application file for complete search history.

(56) References Cited

U.S. PATENT DOCUMENTS

2006/0171578 A1*   8/2006   Novak ...................... G06T 7/30
                                                         600/407
2010/0119041 A1    5/2010   Ohara
2011/0311032 A1   12/2011   Miller
(Continued)

FOREIGN PATENT DOCUMENTS

CN       102429673 A      5/2012
CN       102783969 A     11/2012
(Continued)

OTHER PUBLICATIONS

European Search Report issued in counterpart European Patent Application No. EP 22205907.3, dated Sep. 7, 2023.
(Continued)

*Primary Examiner* — Chih-Cheng Kao
(74) *Attorney, Agent, or Firm* — Westbridge IP LLC

(57) ABSTRACT

Disclosed are a method and a system for visualizing X-ray positioning of a handheld X-ray machine. The method includes: acquiring video acquisition information and distance information from a preset distance acquisition module to an image receiving surface; processing the video acquisition information and the distance information and generating a processing result; and presenting a projection area of the X-ray based on the processing result.

6 Claims, 5 Drawing Sheets

(56) References Cited

U.S. PATENT DOCUMENTS

| | | | |
|---|---|---|---|
| 2016/0174918 A1* | 6/2016 | Wang | A61B 6/467 378/150 |
| 2016/0232945 A1 | 8/2016 | Chen et al. | |
| 2017/0337681 A1 | 11/2017 | Lure et al. | |
| 2021/0330275 A1* | 10/2021 | Chen | A61B 6/544 |

FOREIGN PATENT DOCUMENTS

| | | |
|---|---|---|
| CN | 103163163 A | 6/2013 |
| CN | 203776919 U | 8/2014 |
| CN | 105956386 A | 9/2016 |
| CN | 107242880 A | 10/2017 |
| CN | 108392214 A | 8/2018 |
| CN | 109091118 A | 12/2018 |
| CN | 110033465 A | 7/2019 |
| CN | 110084753 A | 8/2019 |
| CN | 110389494 A | 10/2019 |
| CN | 110974294 A | 4/2020 |
| CN | 111182280 A | 5/2020 |
| CN | 111528880 A | 8/2020 |
| CN | 112836656 A | 5/2021 |
| CN | 113180716 A | 7/2021 |
| CN | 114343689 A | 4/2022 |
| JP | 2012075644 A | 4/2012 |
| JP | 2016097225 A | 5/2016 |
| WO | 2011130198 A2 | 10/2011 |
| WO | 2018053262 A1 | 3/2018 |
| WO | 2018056563 A1 | 3/2018 |
| WO | 2020189940 A2 | 9/2020 |

OTHER PUBLICATIONS

First Office Action issued in counterpart Chinese Patent Application No. 202210413517.8, dated May 31, 2022.

Notification to Grant Patent Right for Invention issued in counterpart Chinese Patent Application No. 202210413517.8, dated Jun. 29, 2022.

* cited by examiner

METHOD AND SYSTEM FOR VISUALIZING X-RAY POSITIONING OF HANDHELD X-RAY MACHINE

CROSS-REFERENCE TO RELATED APPLICATIONS

This application claims priority to Chinese Patent Application No. 202210413517.8, filed on Apr. 20, 2022, the entire disclosure of which is incorporated herein by reference.

TECHNICAL FIELD

The present disclosure relates to the technical field of X-ray machine application, and in particular to a method and a system for visualizing X-ray positioning of a handheld X-ray machine.

BACKGROUND

An X-ray machine is a device for generating X-rays, which is mainly composed of an X-ray tube, an X-ray machine power supply and a control circuit. The X-ray tube includes a cathode filament, an anode target and a vacuum glass tube. The X-ray machine power supply can be divided into high-voltage power supply and filament power supply, in which the filament power supply is configured to heat the filament, and the high-voltage output terminals of the high-voltage power supply are respectively clamped at both ends of the cathode filament and the anode target, providing a high-voltage electric field to accelerate the active electrons on the filament to flow to the anode target to form a high-speed electron flow. After bombarding the surface of the anode target, 99% of the electrons are converted into thermal energy, and 1% of the electrons generate X-ray due to bremsstrahlung projection.

Traditional handheld X-ray machines are positioned by light field beam limiters, cone beam limiters and cylindrical beam limiters. At present, the current X-ray positioning methods are all positioned through the field of view of visible light. Only by being close to the beam limiter can the operator of the X-ray machine see the area of the light field beam and locate the X-ray area.

In view of the above-mentioned related art, the applicant considers that it is inconvenient for the operator to know the size of the X-ray area on the worktable in real time and to locate the X-ray area.

SUMMARY

In order to facilitate the operator to know the size of the X-ray area in real time, thereby facilitating the operator to locate the X-ray, the present disclosure provides a method and a system for visualizing X-ray positioning of a handheld X-ray machine.

The present disclosure provides a method for visualizing X-ray positioning of a handheld X-ray machine, including:
  acquiring video acquisition information, and distance information from a preset distance acquisition module to an image receiving surface;
  processing the video acquisition information and the distance information and generating a processing result; and
  presenting a projection area of the X-ray based on the processing result.

When a patient needs to be irradiated with X-ray, the image information of the lesion area is collected by the camera module, and then the distance information from a distance acquisition module to an image receiving surface is obtained; the X-ray is restrained within a certain area through the restraint effect of the beam limiter module on the X-ray; then, calculating the projection area in the image receiving surface projected by the X-ray, with the distance information from the focus of the camera module to the image receiving surface; the projection area is presented by the image information obtained by the camera module. By adopting the above technical solution, the X-ray area can be seen without approaching the beam limiter module, which is easy for the operator to know the size of the X-ray area and locate the X-ray.

In some embodiments, the operation of processing the video acquisition information and the distance information and generating a processing result includes:
  acquiring current X-ray restraint mode information; and
  calculating the projection area of the X-ray and generating a processing result based on the current X-ray restraint mode information and the distance information.

By adopting the above technical solution, the beam limiter module can adjust the degree of X-ray divergence by adjusting its own X-ray restraint mode. For example, since the cone beam limiter has multiple area options such as 43*43 cm, 35*35 cm, 10*10 cm and so on within a 1.5-meter X-ray field of view, under a fixed distance, different projection areas of the X-ray can be adjusted according to different working conditions.

In some embodiments, the projection area includes a first area and a second area that are spliced together, the first area is configured to display an X-ray projection area of human body, and the second area is configured to display an image area of the outer surface of human body.

By adopting the above technical solution, when photographing the upper body organs of the patient, the bone organs and the external position of the body under the X-ray are observed through a first area and a second area which are spliced together. Thus, it can be observed which position of the bone organ actually corresponds to the outside of the human body, which facilitates medical staffs to observe the patient's condition.

In some embodiments, the operation of presenting a projection area of the X-ray includes:
  acquiring organ characteristic information in the first area based on the X-ray projection area of human body displayed in the first area;
  acquiring an integrity of the organ characteristic based on the organ characteristic information in the first area;
  determining whether the integrity of the organ characteristic reaches a preset threshold value of the integrity; and
  increasing the first area and adaptively decreasing the second area in response that the integrity of the organ characteristic does not reach the preset threshold value.

By adopting the above technical solution, in the process of photographing, if the window area of the display screen is divided by the central axis, half of the area displays the organ characteristic under X-ray, and half of the area displays the image outside the human body, and the area of the X-ray field of view is adaptively adjusted according to the observation condition, so that medical staffs can observe the condition of the entire organ under X-ray field of view.

In some embodiments, after the operation of presenting a projection area of the X-ray, the method further includes:

acquiring image information representing the projection area of the X-ray;

capturing bone organ characteristic information based on the image information;

acquiring a matching degree of the bone organ characteristic information and a preset bone organ characteristic boundary model;

determining whether the matching degree reaches a preset threshold value of the matching degree; and issuing a warning in response that the matching degree does not reach the threshold value of the matching degree.

By adopting the above technical solution, in the process of photographing, by matching the image information captured by the camera with the original boundary model, the orientation and display position of the captured image information can be compared and corrected, which can reduce the occurrence of image skew. Besides, boundary model can be horizontal, vertical, and boundary lines.

In some embodiments, after the operation of issuing a warning in response that the matching degree does not reach the threshold value of the matching degree, the method further includes:

acquiring warning time information; and controlling a preset correction module to adjust a preset camera module to make the matching degree reach the preset threshold value of the matching degree, in response that the warning time reaches a preset threshold value of the warning time.

By adopting the above technical solution, when the current matching degree does not reach the preset threshold value of the matching degree, it means that the captured image does not reach a suitable photographing angle or the captured image is skewed. When this situation persists, correction is required for better X-ray image acquisition. Therefore, during correction, when the warning time exceeds the threshold value, the camera module needs to be automatically adjusted so that the camera module can obtain relatively standard X-ray images.

The present disclosure provides a system for visualizing X-ray positioning of a handheld X-ray machine, applied to the above method for visualizing X-ray positioning of a handheld X-ray machine, includes: an X-ray emission module, a camera module, a distance acquisition module, a processing module and a display module.

The camera module is configured to acquire video acquisition information.

The distance acquisition module is configured to acquire the distance information from the focus of the camera module to an image receiving surface.

The processing module is configured to process the video acquisition information and the distance information and generate a processing result.

The display module is configured to present a projection area of the X-ray based on the processing result.

When a patient needs to be irradiated with X-ray, the image information of the lesion area is collected by the camera module, and then the distance information from a distance acquisition module to an image receiving surface is obtained; the X-ray is restrained within a certain area through the restraint effect of the beam limiter module on the X-ray; then, calculating the projection area in the image receiving surface projected by the X-ray, with the distance information from the focus of the camera module to the image receiving surface; the projection area is presented by the image information obtained by the camera module. By adopting the above technical solution, the X-ray area can be seen without approaching the beam limiter module, which is easy for the operator to know the size of the X-ray area and locate the X-ray.

In some embodiments, the system further includes a beam limiter module.

The beam limiter module is configured to adjust the current X-ray restraint mode, to adjust the projection area of the X-ray.

By adopting the above technical solution, the beam limiter module can adjust the degree of X-ray divergence by adjusting its own X-ray restraint mode. For example, since the cone beam limiter has multiple area options such as 43*43 cm, 35*35 cm, 10*10 cm and so on within a 1.5-meter X-ray field of view, under a fixed distance, different projection areas of the X-ray can be adjusted according to different working conditions.

To sum up, the present disclosure includes the following beneficial technical effects:

1. The projection area in the image receiving surface projected by the X-ray can be calculated according to the distance information from the focus of the camera module to the image receiving surface, and then the projection area is presented by the image information obtained by the camera module. Therefore, the X-ray area can be seen without approaching the beam limiter module, which is easy for the operator to know the size of the X-ray area and to locate the X-ray;

2. The bone organs and the external position of the body under the X-ray are observed through a first area and a second area which are spliced together. Thus, it can be observed which position of the bone organ actually corresponds to the outside of the human body, which is convenient for medical staffs to observe the patient's condition.

DETAILED DESCRIPTION OF THE EMBODIMENTS

The present disclosure will be further described in detail below with reference to FIGS. 1-7.

Figure 1:
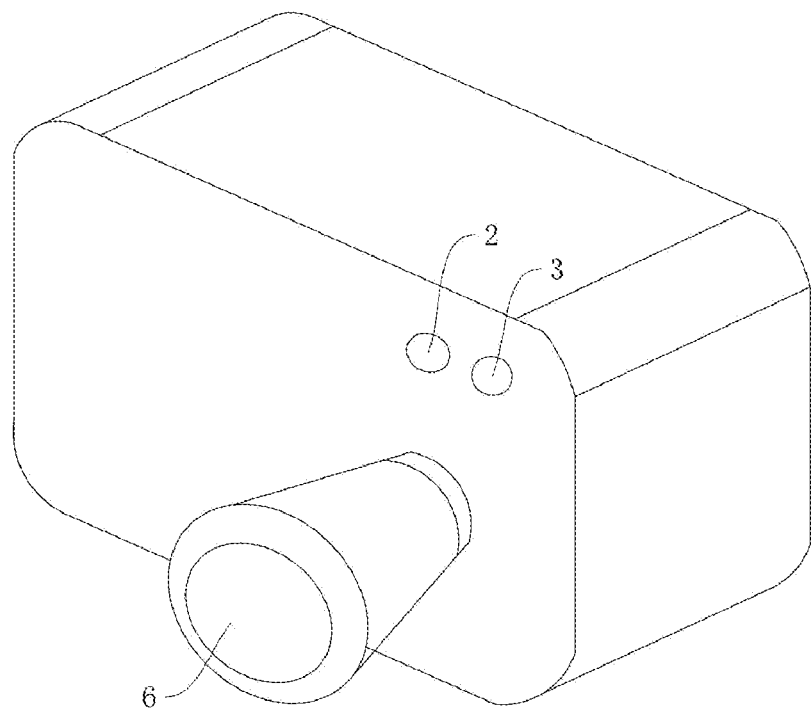
FIG. 1 is a schematic structural diagram of the overall structure of a system for visualizing X-ray positioning of a handheld X-ray machine according to an embodiment of the present disclosure.
Figure 2:
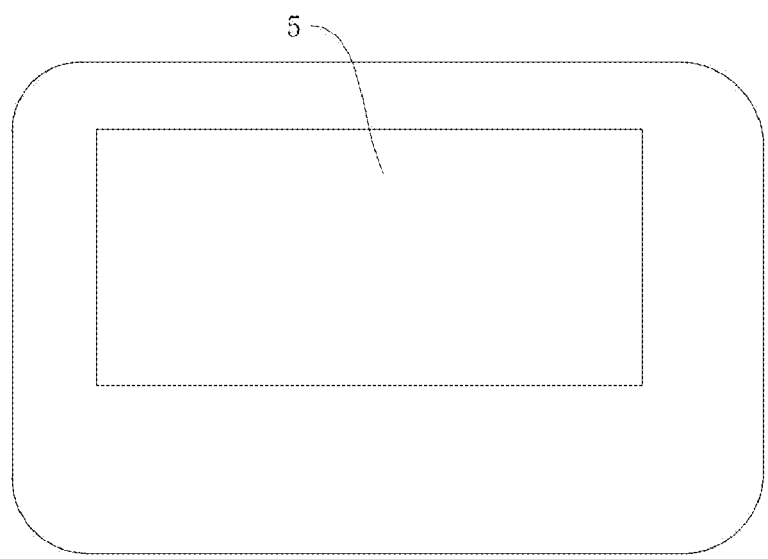
FIG. 2 is another schematic structural diagram of the overall structure of a system for visualizing X-ray positioning of a handheld X-ray machine according to an embodiment of the present disclosure.

An embodiment of the present disclosure provides a system for visualizing X-ray positioning of a handheld X-ray machine. Referring to FIG. 1 and FIG. 2, FIG. 1 is a schematic structural diagram of the overall structure of a system for visualizing X-ray positioning of a handheld X-ray machine according to an embodiment of the present disclosure, and FIG. 2 is another schematic structural diagram thereof. The system includes a camera module 2, a distance acquisition module 3, a display module 5 and a beam limiter module 6.

Figure 3:
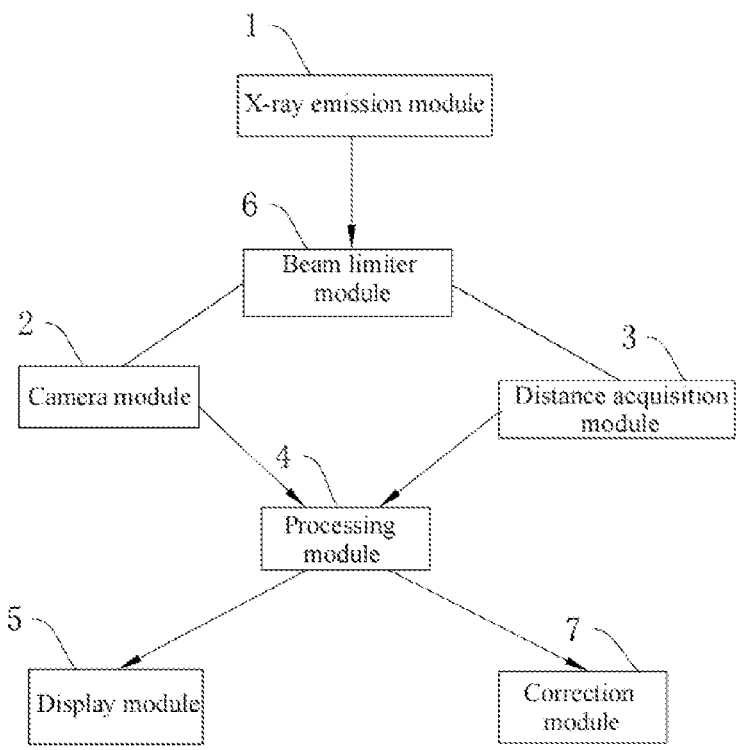
FIG. 3 is a hardware architecture schematic diagram of a system for visualizing X-ray positioning of a handheld X-ray machine according to an embodiment of the present disclosure.

Referring to FIG. 3, the system further includes an X-ray emission module 1 and a processing module 4.

The camera module 2 is for acquiring video acquisition information; the camera module 2 includes, but is not limited to, a webcam, a line scan camera, and other devices with a video recording function.

The distance acquisition module 3 is for acquiring the distance information from a focus of the camera module 2 to an image receiving surface (SID). It can be a distance meter, or an ultrasonic sensor, etc. For example, the distance obtained by the distance meter is 1 meter, 1.5 meters, and so on.

The processing module 4 is for processing the video acquisition information and the distance information and generate a processing result. It can be electronic components such as chips and processors that enable the X-ray machine to perform visualizing X-ray positioning.

The display module 5 is for presenting a projection area of the X-ray based on the processing result. It can be an LED display screen, an LCD panel and so on.

The ultrasonic sensor is mainly for collecting the distance signal from the focus to the image receiving surface. The signal is processed by the processing module 4, and then the video area which is equivalent to the area of the X-ray field of view is displayed in the display module 5. This operation allows the operator to perceive the area of the X-ray field of view. That is, the visible video area is the area of the X-ray field of view.

The beam limiter module 6 adjusts the current X-ray restraint mode by itself and restrains the X-ray within a certain area to prevent the scattering of the X-ray.

Figure 4:
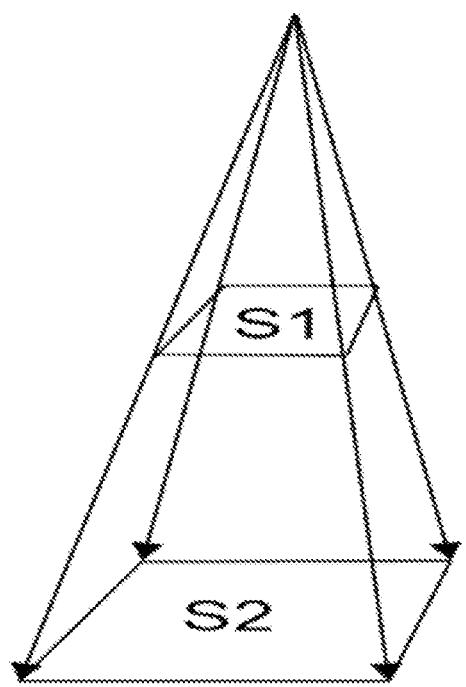
FIG. 4 is a working schematic diagram of the beam limiter module in FIG. 1.

Referring to FIG. 4, if it is known that when the SID is 1 meter, the area of the X-ray field of view of the cone beam limiter is S1; when the SID is 1.5 m, the area of the X-ray field of view of the cone beam limiter is S2. The software algorithm automatically adjusts the area visible in the video area of view based on the known area of the X-ray field of view at different distances to achieve consistency between the video area and the X-ray field of view.

For example, when the operator takes a chest X-ray with a handheld X-ray machine, the cone beam limiter can cover an X-ray field of view of 43*43 cm when the SID is 1.5 m, and the video signal captured by the camera is also displayed on the screen in a 43*43 cm area, achieving consistency between the X-ray field of view and video area of view. It facilitates the operator to locate the X-ray area in real time to prevent incomplete shooting of the shooting area, or unnecessary projection of the patient due to the X-ray field of view being larger than the shooting area.

The camera captures the video signal and the ultrasound sensor also captures the distance signal from the focus to the image receiving surface. After these two kinds of signals are calculated by the algorithm of the processing module 4, the area of the X-ray field of view at the current distance can be determined, and then the screen is controlled to display the area of the X-ray field of view. So, with this operation, the video area that the operator can see is the area covered by the X-ray field of view.

How to achieve consistency between the video area and the area of the X-ray field of view:

1. because the cone beam limiter restrains the area of the X-ray field of view, the area of the X-ray field of view is fixed at the SIDs with different distances (distances from the focus to the image receiving surface);
2. the focus and angle of view of the camera are changeable and can be adjusted to a field of view consistent with the X-ray field of view, thus achieving a video field of view consistent with the X-ray field of view;
3. using software to adjust the focal length of the camera and the size of the area of the field of view. The algorithm can adjust the area of the video field of view according to the known X-ray range of different SIDs of the cone beam limiter.

This embodiment simply illustrates a cone beam limiter with an X-ray field of view that corresponds to each other at different SIDs. A similar beam limiter using motors or manually adjustable gear is also within the scope of protection of this disclosure. For example, the SID of a cone beam limiter at an X-ray field of view of 1.5 m, whose coverage is 43*43 cm, 35*35 cm or 10*10 cm and so on can also be achieved by adopting this solution.

The implementation principle of the system for visualizing X-ray positioning of a handheld X-ray machine in this embodiment of the present disclosure is as follows:

When the system works, adjust the mode of the beam limiter module 6 and acquire the straight line distance between the focus of the camera module 2 and the projection area. Then calculate the projection area of the X-ray according to the mode of the beam limiter module 6, and display this area on display module 5. It facilitates the operator of the handheld X-ray machine to quickly locate the area of the X-ray field of view, which can improve the image quality and reduce the radiation area of the patient.

Figure 5:
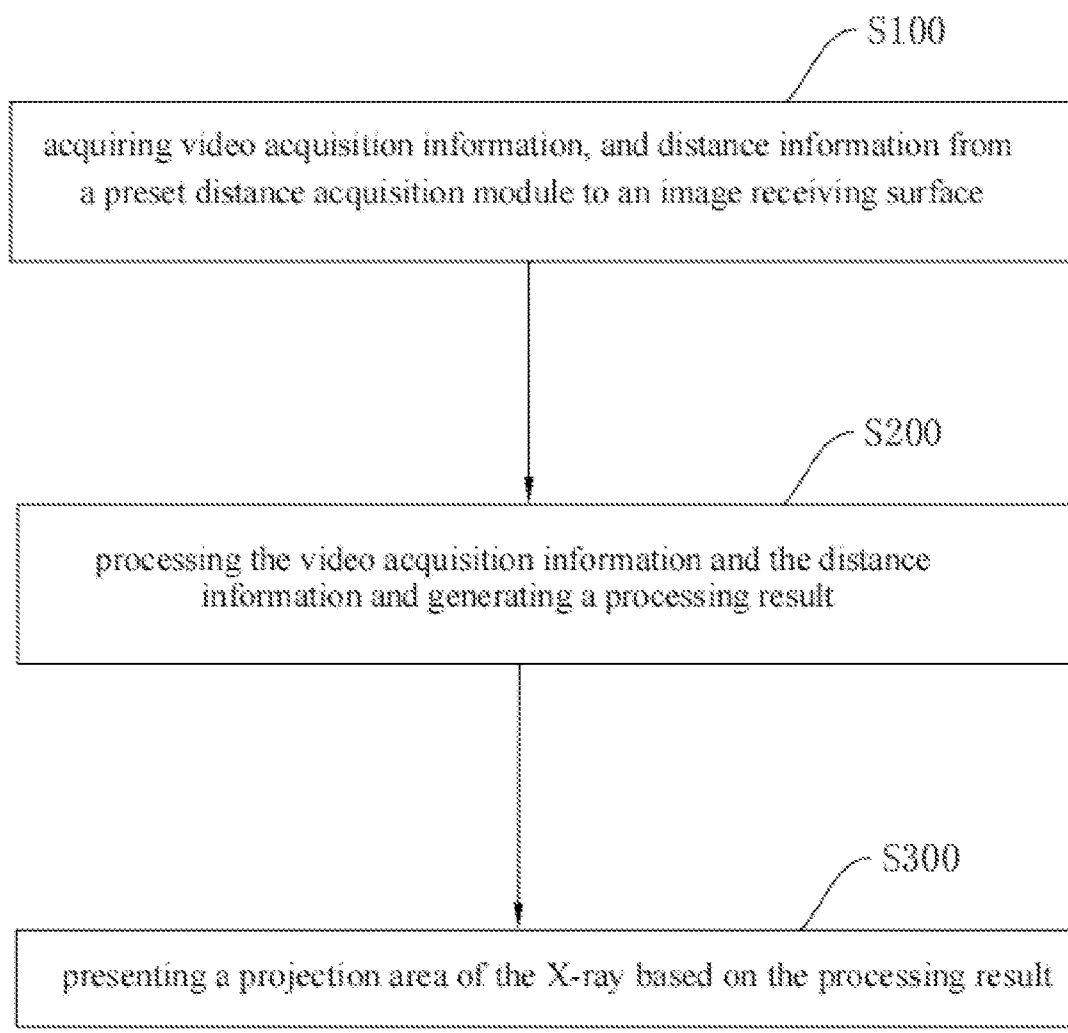
FIG. 5 is a schematic flowchart of a method for visualizing X-ray positioning of a handheld X-ray machine according to an embodiment of the present disclosure.

Based on the above hardware architecture, referring to FIG. 5, an embodiment of this present disclosure further discloses a method for visualizing X-ray positioning of a handheld X-ray machine, which includes S100 to S300.

S100: acquiring video acquisition information, and distance information from a preset distance acquisition module 3 to an image receiving surface.

While the camera module 2 acquires the video image, the distance acquisition module 3 acquires the distance information from the focus of the camera module 2 to the image receiving surface (SID). The distance acquisition module 3 can be a distance meter, for example, the distance obtained by the distance meter is 1 meter, 1.5 meters, and so on.

S200: processing the video acquisition information and the distance information and generating a processing result.

Acquiring a projection area of the X-ray at a certain distance according to a preset operation program of the processing module 4 and the restraining effect of the beam limiter module 6 on the X-ray.

S300: presenting a projection area of the X-ray based on the processing result.

The projection area of the X-ray is captured by the camera module 2 based on the projection area of the X-ray, then the projection area of the X-ray is displayed by the display module 5.

This embodiment simply illustrates a cone beam limiter with an X-ray field of view that corresponds to each other at different SIDs. A similar beam limiter using motors or manually adjustable gear is also within the scope of protection of this disclosure. For some common beam limiters, the coverage of the X-ray field of view can be adjusted under the same SID. For example, the SID of a cone beam limiter at an X-ray field of view of 1.5 m, whose coverage is 43*43 cm, 35*35 cm or 10*10 cm and so on can also be achieved by adopting this solution.

Figure 6:
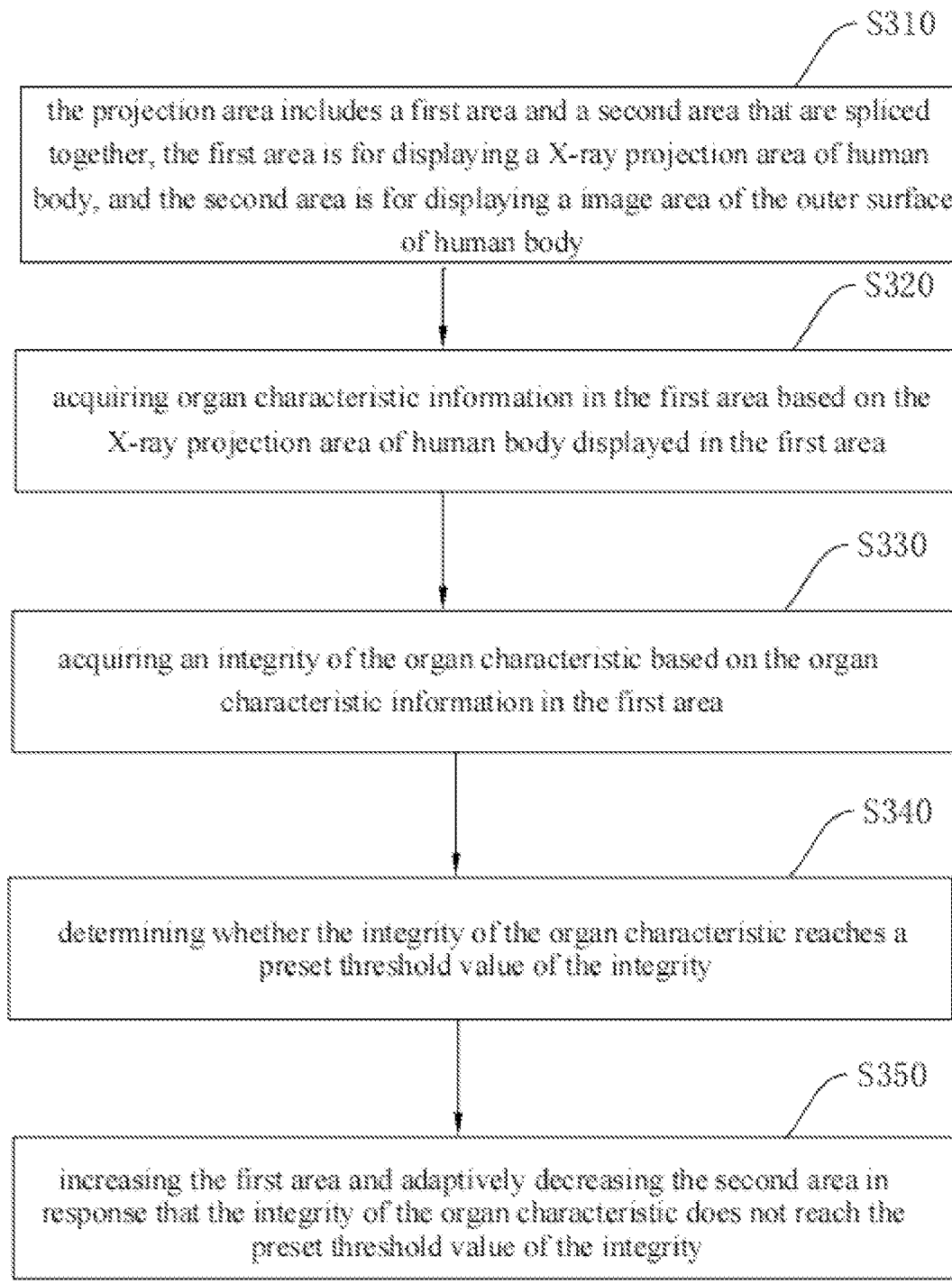
FIG. 6 is an expanded schematic flowchart of the operation S300 in FIG. 4.

Referring to FIG. 6, S300 also includes S310 to S320.

S310: the projection area includes a first area and a second area that are spliced together, the first area is for displaying an X-ray projection area of human body, and the second area is for displaying an image area of the outer surface of human body.

When photographing the upper body organs of the patient, the bone organs and the external position of the body under the X-ray are compared through a first area and a second area which are spliced together. For example, the left side of the central axis of the screen represents the image outside the human body, and the right side represents the bone and organ images under X-ray. It facilitates medical staffs to observe which position of the bone and organ actually corresponds to the outside of the human body and observe the patient's condition.

S320: acquiring organ characteristic information in the first area based on the X-ray projection area of human body displayed in the first area.

S330: acquiring an integrity of the organ characteristic based on the organ characteristic information in the first area.

S340: determining whether the integrity of the organ characteristic reaches a preset threshold value of the integrity.

S350: increasing the first area and adaptively decreasing the second area in response that the integrity of the organ characteristic does not reach the preset threshold value of the integrity.

In the process of photographing, when the window area of the display screen is divided by the central axis, half of the area displays the organ characteristic under X-ray, and half of the area displays the image outside the human body. If the organ to be observed is not fully displayed under X-ray, the area of the X-ray field of view needs to be adaptively adjusted according to the observation condition, so that medical staffs can observe the condition of the entire organ under X-ray field of view. Referring to one example, in an initial state, the size of the first area is 9 cm*15 cm, and the size of the second area is also 9 cm*15 cm. When the preset integrity threshold value is 90%, but only 70% of the complete organ features can be seen in the first area, in this situation, the sizes of the first area and the second area need to be adjusted. After adjustment, the size of the first area is 12 cm*15 cm, and the size of the second area is 6 cm*15 cm, which helps to display the complete organ image to be observed in the first area as much as possible.

Figure 7:
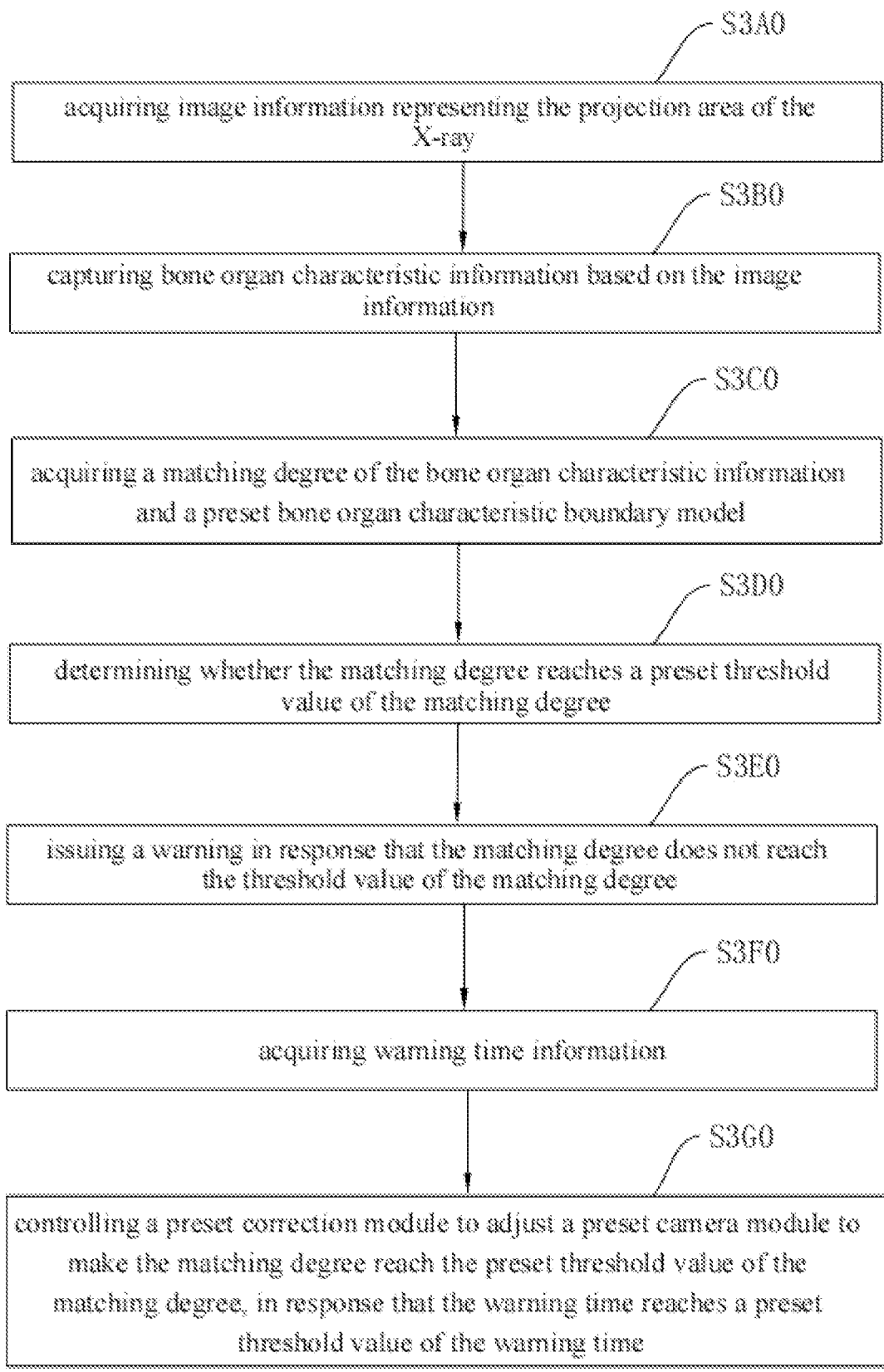
FIG. 7 is a schematic flowchart after the operation S300 in FIG. 4.

Referring to FIG. 7, the operations after S300 include S3A0 to S3G0.

S3A0: acquiring image information representing the projection area of the X-ray.

S3B0: capturing bone organ characteristic information based on the image information.

S3C0: acquiring a matching degree of the bone organ characteristic information and a preset bone organ characteristic boundary model.

In the process of photographing, by matching the image information captured by the camera with the original boundary model, the orientation and display position of the captured image information can be compared and corrected, which can reduce the occurrence of image skew. Besides, boundary model can be horizontal, vertical, and boundary lines.

S3D0: determining whether the matching degree reaches a preset threshold value of the matching degree.

S3E0: issuing a warning in response that the matching degree does not reach the threshold value of the matching degree.

Referring to one example, when the acquired image is always skewed or out of bounds, a warning will be issued. The warning may be an audible and visual warning or a warning in the form of graphic markers on the screen.

S3F0: acquiring warning time information.

S3G0: controlling a preset correction module 7 to adjust a preset camera module 2 to make the matching degree reach the preset threshold value of the matching degree, in response that the warning time reaches a preset threshold value of the warning time.

When the current matching degree does not reach the preset threshold value of the matching degree, it means that the captured image does not reach a suitable photographing angle or the captured image is skewed. When this situation persists, correction is required for better X-ray image acquisition. Therefore, during correction, when the warning time exceeds the threshold value of, for example, 5 s, the camera module 2 needs to be automatically adjusted so that the camera module 2 can obtain relatively standard X-ray images, thereby improving work efficiency. The correction module 7 can be a rotating device arranged on the camera module 2. And the processing module 4 issues a command and controls the rotating device to deflect the camera, so that the main characteristic in the image captured by the camera can be in a more appropriate position.

The above are only some embodiments of the present disclosure, and do not limit the scope of the present disclosure thereto. Under the inventive concept of the present disclosure, any equivalent structural transformations made according to the structure, shape and principle of the present disclosure are included in the scope of the present disclosure.

What is claimed is:

1. A method for visualizing X-ray positioning of a hand-held X-ray machine, comprising:
   acquiring video acquisition information and distance information from a preset distance acquisition module to an image receiving surface;
   processing the video acquisition information and the distance information and generating a processing result; and
   presenting a projection area of the X-ray based on the processing result;
   wherein the projection area comprises a first area and a second area that are spliced together, the first area is configured to display an X-ray projection area of human body, and the second area is configured to display an image area of an outer surface of human body;
   wherein the operation of presenting the projection area of the X-ray comprises:
   acquiring organ characteristic information in the first area based on the X-ray projection area of human body displayed in the first area;
   acquiring an integrity of the organ characteristic based on the organ characteristic information in the first area;
   determining whether the integrity of the organ characteristic reaches a preset threshold value of the integrity; and increasing the first area and adaptively decreasing the second area in response that the integrity of the organ characteristic does not reach the preset threshold value of the integrity.

2. The method of claim 1, wherein the operation of processing the video acquisition information and the distance information and generating the processing result comprises:
    acquiring current X-ray restraint mode information; and
    calculating the projection area of the X-ray and generating the processing result based on the current X-ray restraint mode information and the distance information.

3. The method of claim 1, wherein after the operation of presenting the projection area of the X-ray, the method further comprises:
    acquiring image information presenting the projection area of the X-ray;
    capturing bone organ characteristic information based on the image information;
    acquiring a matching degree of the bone organ characteristic information and a preset bone organ characteristic boundary model;
    determining whether the matching degree reaches a preset threshold value of the matching degree; and
    issuing a warning in response that the matching degree does not reach the threshold value of the matching degree.

4. The method of claim 3, wherein after the operation of issuing the warning in response that the matching degree does not reach the threshold value of the matching degree, the method further comprises:
    acquiring warning time information; and
    controlling a preset correction module to adjust a preset camera module to make the matching degree reach the preset threshold value of the matching degree, in response that the warning time reaches a preset threshold value of the warning time.

5. A system for visualizing X-ray positioning of a handheld X-ray machine, comprising:
    an X-ray emission module;
    a camera module, configured to acquire video acquisition information;
    a distance acquisition module, configured to acquire distance information from a focus of the camera module to an image receiving surface;
    a processing module, configured to process the video acquisition information and the distance information and generate a processing result; and
    a display module, configured to present a projection area of the X-ray based on the processing result;
    wherein the projection area comprises a first area and a second area that are spliced together, the first area is configured to display an X-ray projection area of human body, and the second area is configured to display an image area of an outer surface of human body; and
    wherein the display module is configured to acquire organ characteristic information in the first area based on the X-ray projection area of human body displayed in the first area, acquire an integrity of the organ characteristic based on the organ characteristic information in the first area, determine whether the integrity of the organ characteristic reaches a preset threshold value of the integrity, and increase the first area and adaptively decrease the second area in response that the integrity of the organ characteristic does not reach the preset threshold value of the integrity.

6. The system of claim 5, further comprising:
    a beam limiter module, configured to adjust a current X-ray restraint mode, to adjust the projection area of the X-ray.

* * * * *